(12) United States Patent
Morgan et al.

(10) Patent No.: US 6,501,993 B2
(45) Date of Patent: Dec. 31, 2002

(54) ELECTRODE ASSEMBLY WITH A DETACHABLE DISTAL TIP

(75) Inventors: Kevin L. Morgan, Simi Valley, CA (US); Russell Klehn, Valencia, CA (US); Benedict L. Gomperz, North Hollywood, CA (US); Buehl E. Truex, Glendora, CA (US)

(73) Assignee: Pacesetter, Inc., Sylmar, CA (US)

( * ) Notice: Subject to any disclaimer, the term of this patent is extended or adjusted under 35 U.S.C. 154(b) by 126 days.

(21) Appl. No.: 09/818,418

(22) Filed: Mar. 27, 2001

(65) Prior Publication Data
US 2002/0143379 A1 Oct. 3, 2002

(51) Int. Cl.7 .................................................. A61N 1/05
(52) U.S. Cl. .................................................... 607/122
(58) Field of Search ................................ 600/372–375, 600/377, 381; 606/129; 607/115–116, 119, 122, 126, 128–129

(56) References Cited

U.S. PATENT DOCUMENTS

| | | | |
|---|---|---|---|
| 4,278,093 A | 7/1981 | Lafortune et al. .......... 128/419 |
| 4,350,169 A | 9/1982 | Dutcher et al. ............. 128/783 |
| 5,057,106 A | 10/1991 | Kasevich et al. ............. 606/33 |
| 5,207,683 A | 5/1993 | Goode et al. ............... 606/108 |
| 5,259,394 A | 11/1993 | Bens .......................... 607/127 |
| 5,261,419 A | 11/1993 | Osypka ....................... 607/122 |
| 5,383,922 A | 1/1995 | Zipes et al. ................. 607/122 |
| 5,489,225 A | 2/1996 | Julian ......................... 439/837 |
| 5,545,188 A | 8/1996 | Bradshaw et al. ............. 607/37 |
| 5,807,144 A | 9/1998 | Sivard ......................... 439/816 |
| 5,807,399 A * | 9/1998 | Laske et al. ................. 606/108 |
| 5,851,227 A | 12/1998 | Spehr ......................... 607/126 |
| 5,885,280 A | 3/1999 | Nettekoven et al. .......... 606/41 |
| 5,908,447 A * | 6/1999 | Schroeppel et al. ........ 607/126 |
| 2002/0065543 A * | 11/2000 | Gomperz et al. ........... 607/115 |
| 2002/0123785 A1 * | 9/2002 | Zhang et al. ................ 607/126 |

FOREIGN PATENT DOCUMENTS

DE 3020586 A1 * 3/1981 ............ A61N/1/04

* cited by examiner

Primary Examiner—Kennedy Schaetzle
Assistant Examiner—Kristen Droesch (57) ABSTRACT

An electrode assembly including a tip electrode and a longitudinally extending axially aligned weld electrode egageably receiving a distal end of a coiled wire strand conductor at a proximal end. A connector member includes a fastener having an enlarged head and a threaded shank, the weld electrode includes an integral weld sleeve with an annular locking tab engageable with the enlarged head to prevent longitudinal movement while permitting rotational movement. The weld electrode has an internal bore for receiving an elongated stylet selectively engageable therewith for implanting and explanting the electrode assembly. The tip electrode includes an integral attachment sleeve having an outer peripheral surface extending in a direction away from the tip and having a longitudinally extending tapped bore for engagement with the threaded shank of the connector member. The weld sleeve and attachment sleeve are mutually stepped to prevent their relative rotation when in the locked position.

16 Claims, 6 Drawing Sheets

ELECTRODE ASSEMBLY WITH A DETACHABLE DISTAL TIP

FIELD OF THE INVENTION

The present invention relates to the construction of an electrode assembly for an implantable medical device such as a pacemaker or defibrillator, which enables it to be implanted, then easily explanted when necessary in a manner not previously known.

BACKGROUND OF THE INVENTION

While the present invention will be described in a specific manner as being applicable to a pacemaker, it will be understood that the invention is applicable to any other type of implantable medical device intended to stimulate body tissue. Modem pacemakers monitor the activity of a heart and provide a stimulation pulse in the absence of normal heart activity. Advantageously, such devices are relatively small, lightweight and implantable. In order to sense and stimulate the heart, however, such pacemakers must be used with a pacemaker lead, an electrical conductor that carries electrical signals between the heart and the pacemaker. The pacemaker lead can be inserted into the heart transvenously through a relatively simple and well-known surgical procedure.

Lead extraction is required when an infection occurs and at times when products are upgraded or replaced. When infected leads must be removed, physicians have shown a desire to remove uninfected leads to rid the venous system and right ventricle of unnecessary hardware Current lead extraction techniques have proven adequate but can be time-consuming. The technique of extraction runs a high risk of lead separation. The locking stylet method can run the risk of jamming midway in the lead and is sensitive to inner diameters of leads. Such an occurrence can result in ineffective lead removal or lead separation. The laser extraction method is expensive and not readily available.

For some extractions, removal of the lead body is necessary and extraction of the distal tip is exceedingly difficult because of fibrosis on the myocardium to the tines. Tines are used to fixate and stabilize passive fixation leads. If the distal tip (including tines) were detached, the lead extraction could continue at a low risk.

A number of patents are somewhat definitive of the prior art in this regard. Connector appliances are known for easily and rapidly connecting a lead to an electromedical device, which may be implanted in the body of a recipient and also for disconnecting the lead. Typical of such appliances are U.S. Pat. No. 5,885,280 to Nettekoven et al. for "Electrosurgical Electrode Connector", U.S. Pat. No. 5,807,144 to Sivard for "Device for Affixing a Lead Connector to an Implantable Stimulator", U.S. Pat. No. 5,545,188 to Bradshaw et al. for "Cardiac Pacemaker with Collet-Type Lead Connector", and U.S. Pat. No. 5,489,225 to Julian for "Electrical Terminal with a Collet Grip for a Defibrillator".

More closely akin the present invention are patents, which disclose apparatus for implanting and explanting a distal lead to and from a desired body site. Typical of this group of patents are U.S. Pat. No. 5,261,419 to Osypka for "Cardiac Pacemaker Lead" and U.S. Pat. No. 5,207,683 to Goode et al. for "Apparatus for Removing an Elongated Structure Implanted in Biological Tissue".

It was with knowledge of the foregoing state of the technology that the present invention has been conceived and is now reduced to practice.

SUMMARY OF THE INVENTION

The present invention relates to an electrode assembly for a body implantable lead provided for the delivery of stimulation energy to a desired body site and includes a tip electrode having a face adapted for positioning at least adjacent the desired body site and a longitudinally extending axially aligned weld electrode engageably receiving a distal end of an electrical conductor at a proximal end. The electrical conductor is a coiled wire strand with an inner peripheral surface for fitting reception on an outer peripheral surface of the weld electrode. A connector member includes a fastener having an enlarged head and a threaded shank, the weld electrode includes an integral weld sleeve with an annular locking tab engageable with the enlarged head to prevent longitudinal movement while permitting rotational movement. The weld electrode has an internal bore for receiving an elongated stylet selectively engageable therewith for implanting the electrode assembly at a desired body site and for explanting the electrode assembly from that body site. The tip electrode includes an integral attachment sleeve having an outer peripheral surface extending in a direction away from the face thereof and having a longitudinally extending tapped bore for threaded engagement with the threaded shank of the connector member. The weld sleeve and the attachment sleeve are mutually stepped to prevent their relative rotation when in the locked position. An insulative sheath is fittingly received on the outer peripheral surface of the attachment sleeve and includes a plurality of circumferentially spaced, radially outwardly projecting integral tines.

This invention, then, concerns a lead that has a removable distal electrode which gives the lead the ability to be removed without traumatic surgery. This translates into reduced money and time for the lead extraction procedure. The mechanism is designed for a passive fixation electrode but it can easily be incorporated into an active fixation lead.

The invention is activated by a stylet that has a driver mechanism. In this embodiment, the driver mechanism is a flat blade screwdriver. Standard ball-tip stylets can and are used for implanting the lead and do not affect or activate the driver mechanism.

When a physician has determined that a lead has to be extracted, the first procedure is to pull on the lead to determine whether it can be removed without further surgical procedures. If that is unsuccessful, the physician has the option to detach the distal tip and remove the lead, leaving the tip in the fibrotic growth. This results in shorter time in the operating room and increased safety for the patient. The doctor activates the mechanism by inserting the screwdriver stylet into the lead and advancing the stylet to the most distal position. When that position is reached, the physician then rotates the stylet counterclockwise as if removing a bolt. The stylet engages into the slot of the detachable tip mechanism and further rotation of the stylet results in the tip detaching. The physician then easily extracts the lead.

It is a feature of the present invention to provide the construction of an electrode assembly for an implantable medical device such as a pacemaker or defibrillator, which enables it to be implanted, then easily explanted when necessary.

It is a further feature of the present invention to provide a surgeon with the option, in one instance, of extracting both the lead and the tip electrode if possible without undue harm to the surrounding tissue and, in another instance, of extracting only the lead, leaving the tip electrode in the fibrotic growth which impedes its removal.

Still a further feature of the present invention is to provide such an electrode assembly with a highly removable tip electrode for safer and less costly lead explants.

Yet a further feature of the present invention is to provide such an electrode assembly with a construction which activates with a special driver stylet.

A still further feature of the present invention is to provide such an electrode assembly with a lead, which becomes isodiametric for easy removal.

Yet another further feature of the present invention is to provide such an electrode assembly with a construction which handles like a standard RV lead at implant.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENT

As earlier explained, hearts having pacing leads implanted occasionally become infected. This infection may or may not be cleared up with antibiotic therapy. When the therapy is refractory, the lead must be removed. Many times this procedure requires surgery and endangers the patient. In other situations, patients may have exit block or leads that are superfluous. It would be a benefit to the patient to have the leads removed if there was little risk to the patient.

Fibrosis is the healing mechanism of the body. When a lead is implanted, it is encapsulated with this fibrotic growth.

On passive fixation leads tines are placed on the distal tip to fixate and stabilize the lead. If the lead is to be removed, the tines must be removed from the fibrotic growth to free up the lead.

Figure 1:
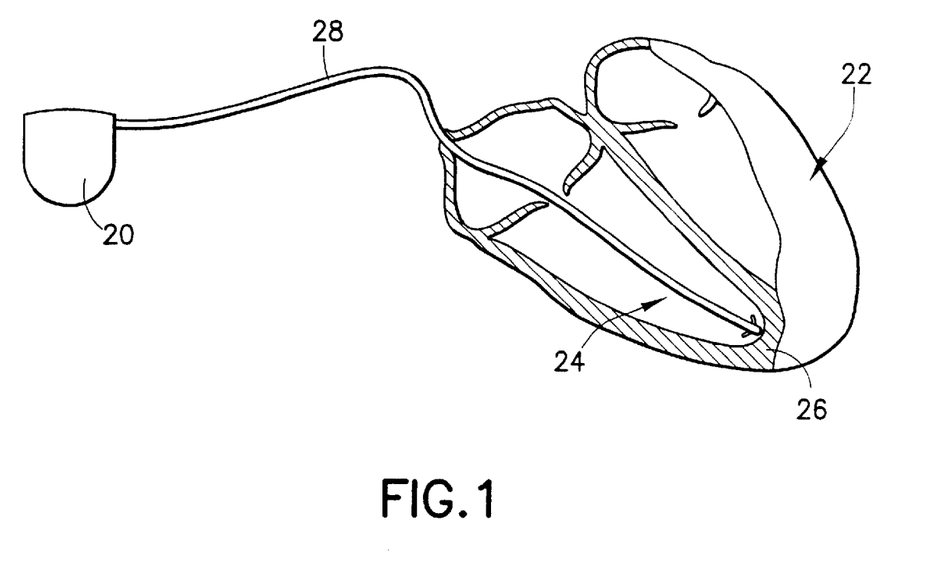
FIG. 1 is a diagrammatic elevation view, partly cut away and in section illustrating a pacemaker which is electrically connected to a selected site of a heart for stimulation and utilizing the benefits of the present invention.

With this as background, refer now to FIG. 1 which illustrates a cardiac pacemaker 20 for stimulating a heart 22, and a novel and improved electrode assembly 24 for the delivery of stimulation energy to a desired body site 26. A body implantable lead 28 connects the pacemaker 20 and the electrode assembly 24. Although the present invention will be described with reference to the embodiments shown in the drawings, it should be understood that the present invention can be embodied in many alternate forms of embodiments. In addition, any suitable size, shape or type of elements or materials could be used.

Figure 2:
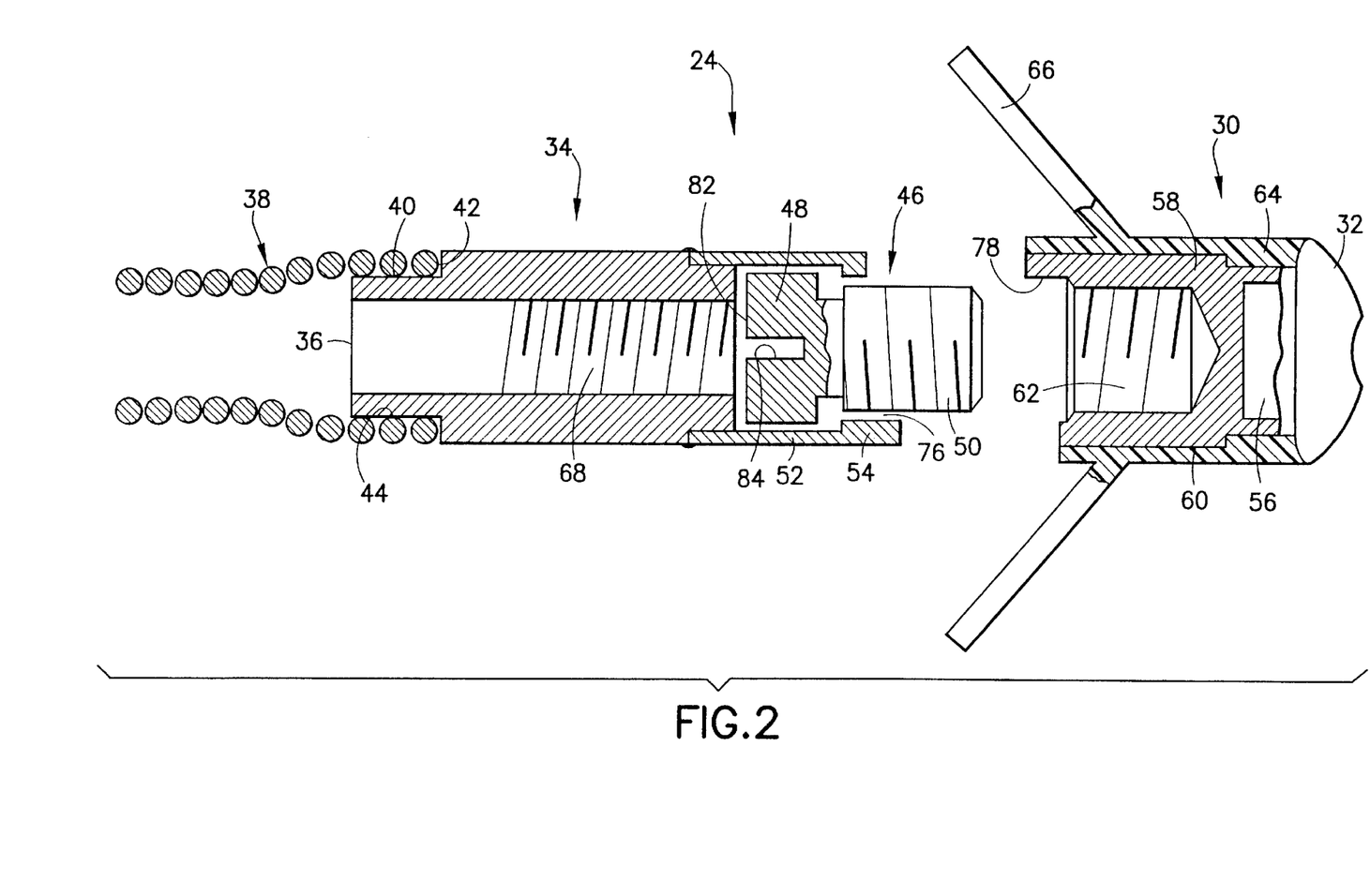
FIG. 2 is a partially exploded side elevation view, largely cut away and in section, of an electrode assembly embodying the present invention.
Figure 3:
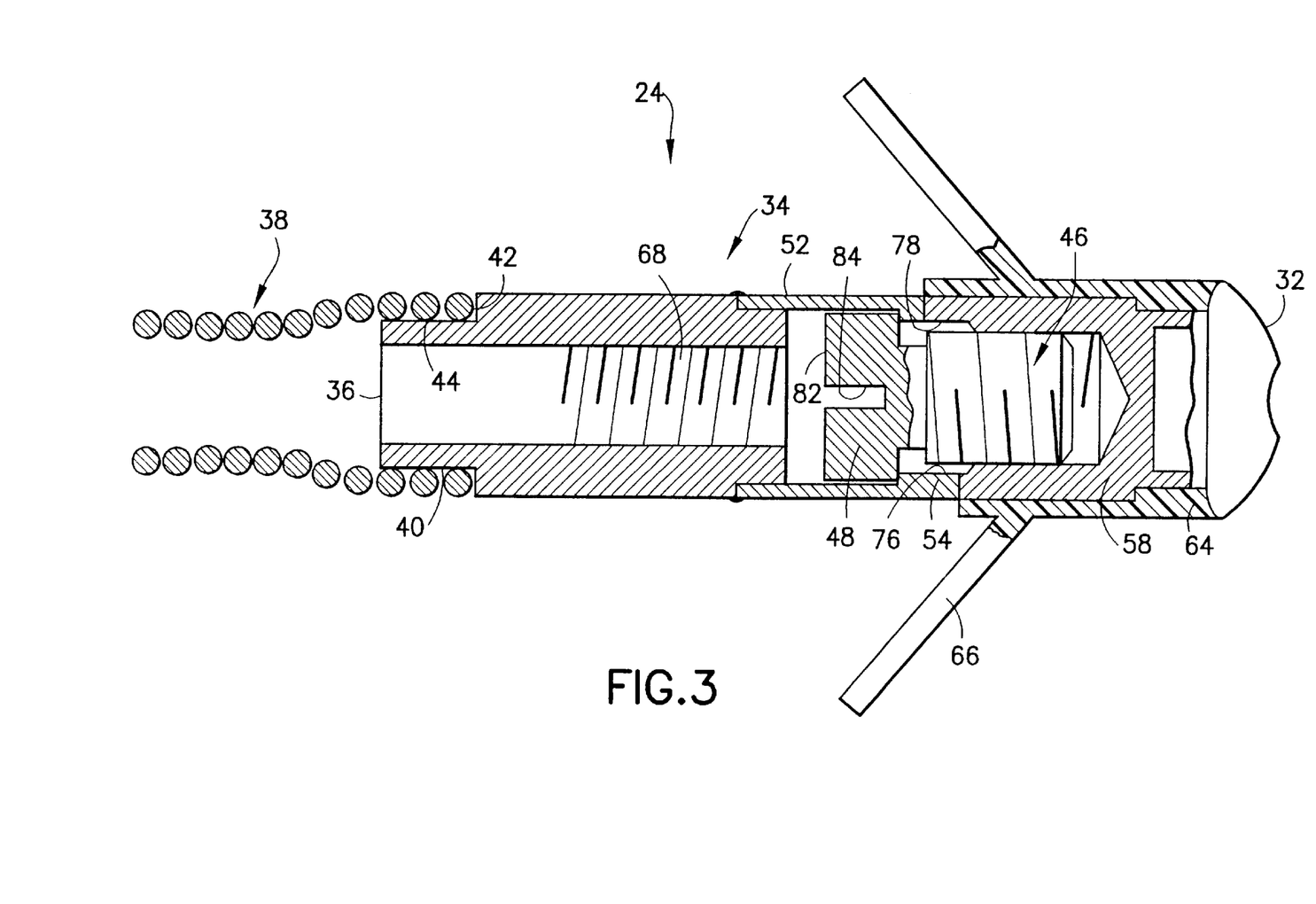
FIG. 3 is a side elevation view, in section, of the electrode assembly of FIG. 2 in its assembled condition.

Turning now to FIGS. 2 and 3, the electrode assembly 24 is seen to include a tip electrode 30 having a face 32 adapted for positioning at least adjacent the desired body site 26. A longitudinally extending weld electrode 34 is axially aligned with the tip electrode 30 and at a proximal end 36 engageably receives one end of an electrical conductor 38 within the lead 28. More specifically, at its proximal end 36, the weld electrode 34 has an annular recessed outer peripheral surface 40 and, typically, the electrical conductor 38 is a coiled wire strand having a distal end 42 with an inner peripheral surface 44 for fitting reception on the outer peripheral surface of the weld electrode. With the elongated coiled electrical conductor 38 thus coaxially received on, and attached to, the weld electrode 34, a connection is thereby obtained for achieving electrical continuity between the tip electrode 30 and the electrical conductor when the weld electrode and the tip electrode are in the locked position in the manner to be described below.

A connector member in the form of a fastener 46 having an enlarged head 48 and a threaded shank 50 extending away from the enlarged head is movably mounted on the weld electrode for selective engagement with the tip electrode and, when so engaged (FIG. 3), for moving the tip electrode longitudinally between an unlocked position (FIG. 2) spaced from the weld electrode and a locked position (FIG. 3) fixed against longitudinal and rotational movement relative to the weld electrode. The weld electrode 34 includes an integral weld sleeve 52 with a radially inwardly directed annular locking tab 54 engageable with the enlarged head 48 to prevent its longitudinal movement with respect to the weld electrode while permitting its rotational movement relative to the weld electrode.

In turn, the tip electrode 30 may include a suitable reservoir 56 for containing a therapeutic drug and an associated delivery system (not shown) to deliver the drug to the body site 26. Regardless, the tip electrode 30 includes an integral attachment sleeve 58 having an outer peripheral surface 60 and extending in a direction away from the face 32. The attachment sleeve has a longitudinally extending tapped bore 62 for threaded engagement with the threaded shank 50 of the connector member or fastener 46.

Continuing to refer to the tip electrode 30, an insulative sheath 64 is fittingly received on the outer peripheral surface 60 of the attachment sleeve 58. A plurality of tines 66 are integral with the insulative sheath 64 and project radially outwardly therefrom, respectively, at a plurality of circumferentially spaced locations. It is also noteworthy that the weld sleeve 52 and the attachment sleeve 58 are mutually stepped, as at 76, 78, respectively, to prevent their relative rotation when in the locked (FIG. 3) position.

Figure 4:
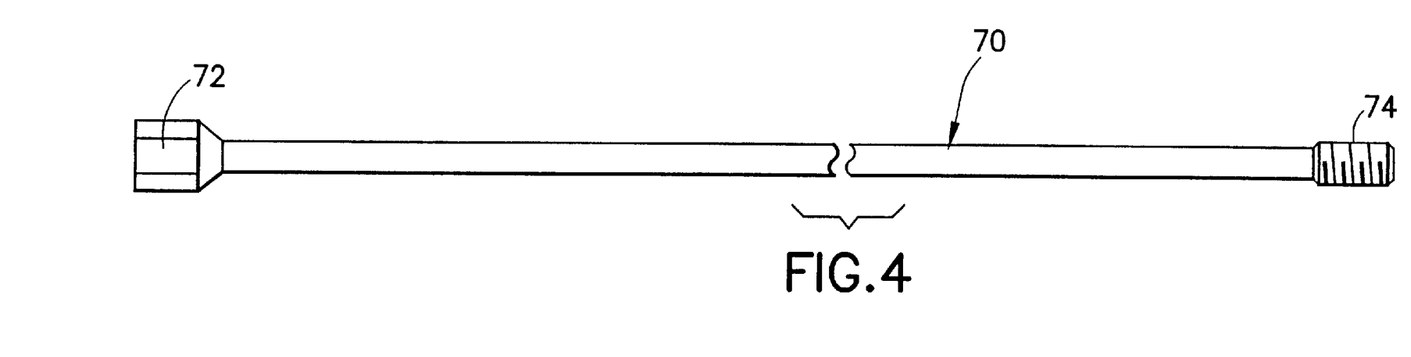
FIG. 4 is a side elevation view of a threaded tip stylet used with the present invention.
Figure 5:
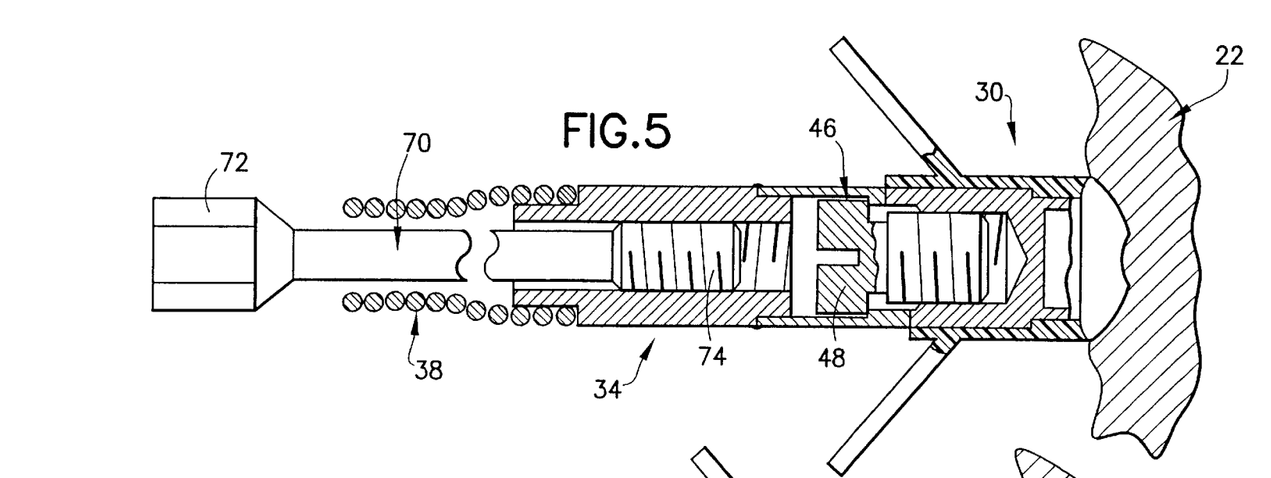
FIGS. 5 and 6 are side elevation views, in section, of the electrode assembly of FIGS. 2 and 3 being operated upon by the threaded tip stylet of FIG. 4 and illustrating two successive positions of the electrode assembly according to the invention.
Figure 6:
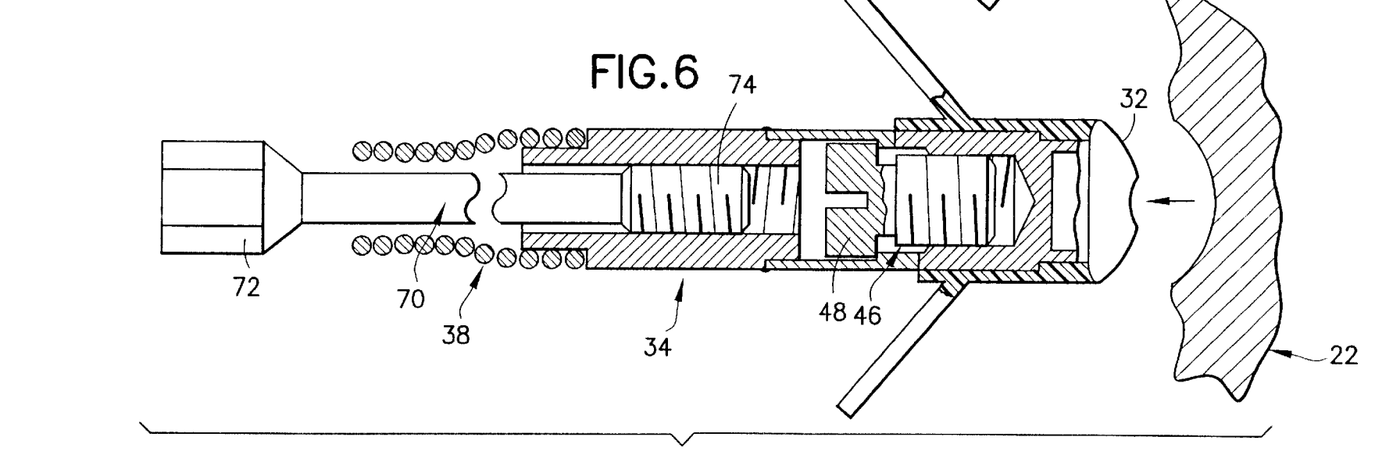

The weld electrode 34 has an internal longitudinally extending tapped bore 68 for receiving an elongated threaded tip stylet 70 (FIG. 4) selectively engageable with the weld electrode 34 for implanting the electrode assembly 24 at the desired body site 26 and for explanting the electrode assembly from that body site. In a known manner, the stylet 70 is flexible but reasonably rigid torsionally with a suitable proximally located operating end 72 and a threaded distal end 74. When the threaded end 74 of the elongated threaded tip stylet 70 which is engaged with the tapped bore 68 of the weld electrode 68 (FIG. 5) and drawn in a proximal direction, in one instance, the entire body assembly (lead 28, weld electrode 34, and tip electrode 30) can be withdrawn from the body site 26 when the weld electrode and the tip electrode are in the locked position (FIG. 6) and, in another instance, the entire body assembly less the tip electrode (that is, lead 28 and weld electrode 34) can be withdrawn from the body site when the weld electrode and the tip electrode are in the unlocked position (as in FIG. 2).

Figure 7:
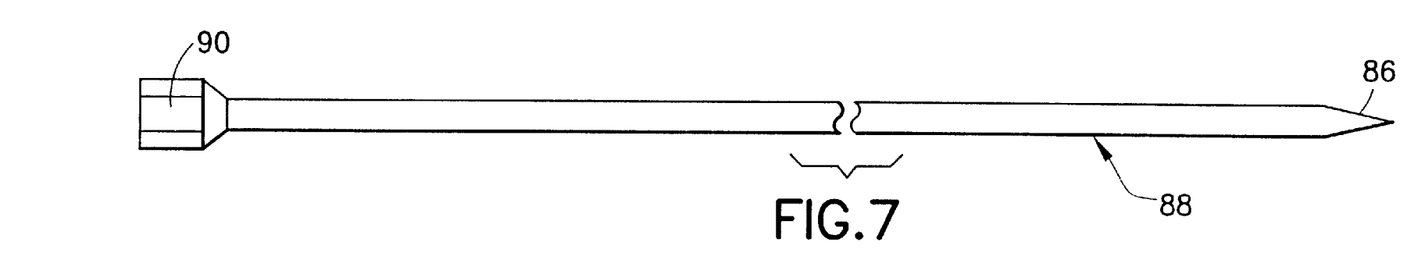
FIG. 7 is a side elevation view of a screwdriver tip stylet used with the present invention.
Figure 8:
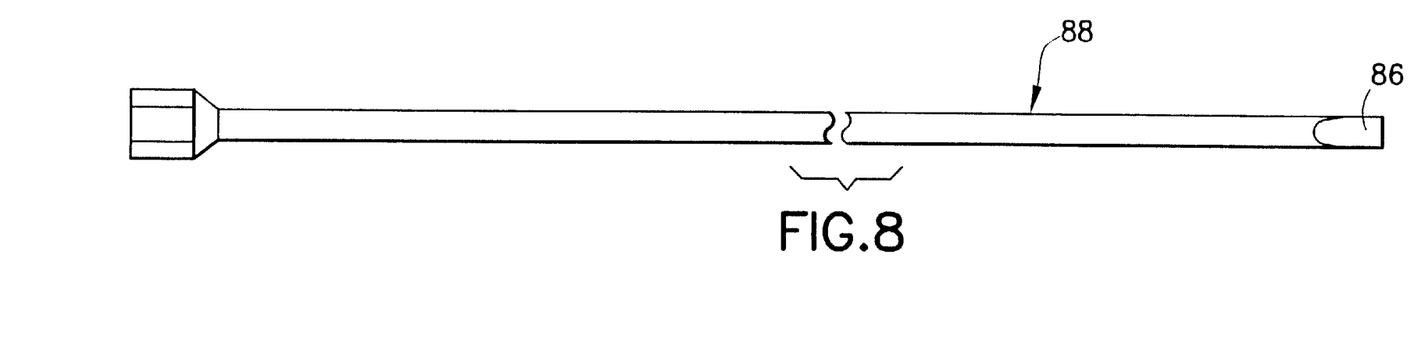
FIG. 8 is a top plan view of the screwdriver tip stylet illustrated in FIG. 7.
Figures 9, 10:
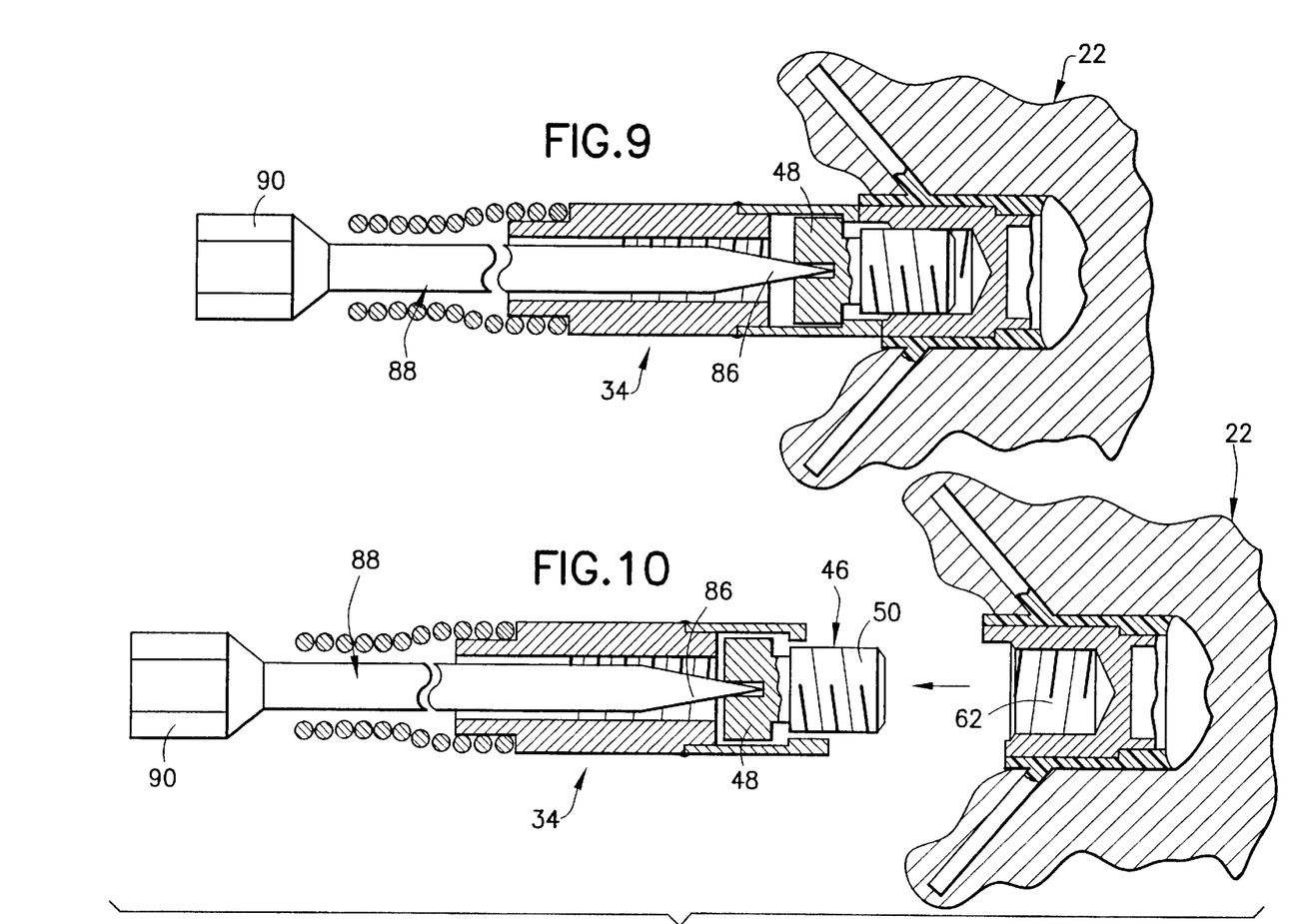
FIGS. 9 and 10 are side elevation views, in section, of the electrode assembly of FIGS. 2 and 3 being operated upon by the screwdriver tip stylet of FIGS. 7 and 8 and illustrating two successive positions of the electrode assembly according to the invention.

The proximal end 82 of the enlarged head 48 of the fastener 46 is formed with a screwdriver engagement component. As illustrated, the head 48 is formed with a slot 84 to receive the tip end of a conventional spade type screwdriver. In this instance, the screwdriver engagement component is adapted to engageably receive the tip end 86 of an elongated screwdriver stylet 88 (FIGS. 7 and 8) which, when so engaged and rotated in one direction, can move the tip electrode longitudinally between the locked position (FIG. 9) and the unlocked position (FIG. 10).

With the construction just described, the goal sought at the outset, namely, the construction of an electrode assembly has been achieved for an implantable medical device such as a pacemaker or defibrillator which enables it to be implanted, then easily explanted when necessary in a manner not previously known. More specifically, this invention incorporates a threaded distal tip to be used with a threaded stylet and a detachable electrode, both for the purposes of improved lead extractability. Both of these ideas have current embodiments for passive fixation leads, but can also be used with active fixation leads.

This new lead extraction system provides a method that mechanically locks into the lead distal tip using the threaded stylet to provide direct force and control at the location where the lead adheres to the myocardium. This will greatly improve lead extractability. Insertion of the threaded stylet into the lead is typical of a standard stylet, but significantly more simple than the locking stylets used today. Direct force and control of the lead tip when explanting leads will eliminate lead fractures and fragments left in the heart.

If the threaded stylet proves to be ineffective in removing the lead or the physician wishes not to risk myocardial injury, detachment of the electrode tip from the lead body may be performed. A screwdriver type of stylet is inserted fully into the lead and engaged into a slot. Then rotating the stylet counterclockwise results in the electrode tip separating from the lead body. The small electrode tip is left encapsulated in fibrotic tissue. The lead is then removed and the myocardium is left unharmed.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An electrode assembly for a body implantable lead for the delivery of stimulation energy to a desired body site comprising:

a tip electrode having a face adapted for positioning at least adjacent the desired body site;

an elongated electrical conductor;

a longitudinally extending weld electrode axially aligned with the tip electrode and at a proximal end engageably receiving one end of the elongated electrical conductor; and a connector member movably mounted on the weld electrode for selective engagement with the tip electrode and, when so engaged, for moving the tip electrode longitudinally between an unlocked position spaced from the weld electrode and a locked position fixed against longitudinal and rotational movement relative to the weld electrode;

the weld electrode having an internal bore for receiving an elongated stylet selectively engageable with the weld electrode for implanting the electrode assembly at a desired body site and for explanting the electrode assembly from that body site.

2. An electrode assembly as set forth in claim 1:

wherein the weld electrode has an outer peripheral surface at its proximal end; and wherein the electrical conductor is a coiled wire strand having a distal end with an inner peripheral surface for fitting reception on the outer peripheral surface of the weld electrode.

3. An electrode assembly as set forth in claim 1:

wherein the connector member includes a fastener having an enlarged head and a threaded shank extending away from the enlarged head;

wherein the weld electrode includes an integral weld sleeve with an annular locking tab engageable with the enlarged head to prevent its longitudinal movement with respect to the weld electrode while permitting its rotational movement relative thereto; and wherein the tip electrode includes an integral attachment sleeve having an outer peripheral surface and extending in a direction away from the face thereof, the attachment sleeve having a longitudinally extending tapped bore for threaded engagement with the threaded shank of the connector member.

4. An electrode assembly as set forth in claim 3:

wherein the weld sleeve and the attachment sleeve are mutually stepped to prevent their relative rotation when in the locked position.

5. An electrode assembly as set forth in claim 3 including:

an elongated coiled electrical conductor coaxially received on the weld electrode and attached thereto to obtain a connection for electrical continuity between the tip electrode and the electrical conductor when the weld electrode and the tip electrode are in the locked position.

6. An electrode assembly as set forth in claim 3 including:

an insulative sheath fittingly received on the outer peripheral surface of the attachment sleeve; and a plurality of tines integral with the insulative sheath and projecting radially outwardly therefrom, respectively, at a plurality of circumferentially spaced locations.

7. An electrode assembly as set forth in claim 1:

wherein the bore of the weld electrode is threaded for threadedly receiving the threaded end of an elongated threaded tip stylet which, when so engaged and drawn in a proximal direction, in one instance, can withdraw from the electrode site the entire body assembly when the weld electrode and the tip electrode are in the locked position and, in another instance, can withdraw from the body site the entire electrode assembly less the tip electrode when the weld electrode and the tip electrode are in the unlocked position.

8. An electrode assembly as set forth in claim 3:

wherein a proximal end of the enlarged head of the fastener is formed with a screwdriver engagement component; and wherein the screwdriver engagement component is adapted to engageably receive a tip end of an elongated screwdriver stylet which, when so engaged and rotated in one direction, can move the tip electrode longitudinally between the unlocked position and the locked position and, when rotated in the opposite direction, can move the tip electrode longitudinally between the locked position and the unlocked position.

9. In combination, an electrode assembly for a body implantable lead for the delivery of stimulation energy to a desired body site comprising:

a tip electrode having a face adapted for positioning at least adjacent the desired body site;

an elongated electrical conductor;

a longitudinally extending weld electrode having an threaded internal bore, the weld electrode being axially aligned with the tip electrode and at a proximal end engageably receiving one end of the elongated electrical conductor; and a connector member movably mounted on the weld electrode for selective engagement with the tip electrode and, when so engaged, for moving the tip electrode longitudinally between an unlocked position spaced from the weld electrode and a locked position fixed against longitudinal and rotational movement relative to the weld electrode; and an elongated threaded tip stylet for use with the electrode assembly being selectively engaged with the threaded bore of the weld electrode for implanting the electrode assembly to a desired body site and for explanting the electrode assembly from that body site.

10. A combination as set forth in claim 9 wherein the weld electrode has an outer peripheral surface at its proximal end; and wherein the electrical conductor is a coiled wire strand having a distal end with an inner peripheral surface for fitting reception on the outer peripheral surface of the weld electrode.

11. The combination as set forth in claim 9:

wherein the connector member includes a fastener having an enlarged head and a threaded shank extending away from the enlarged head;

wherein the weld electrode includes an integral weld sleeve with an annular locking tab engageable with the enlarged head to prevent its longitudinal movement with respect to the weld electrode while permitting its rotational movement relative thereto; and wherein the tip electrode includes an integral attachment sleeve having an outer peripheral surface and extending in a direction away from the face thereof, the attachment sleeve having a longitudinally extending tapped bore for threaded engagement with the threaded shank of the connector member.

12. An electrode assembly as set forth in claim 11:

wherein the weld sleeve and the attachment sleeve are mutually stepped to prevent their relative rotation when in the locked position; and wherein when the threaded tip stylet is so engaged with the threaded bore of the weld electrode and drawn in a proximal direction, in one instance, it can withdraw from the body site the entire electrode assembly when the weld electrode and the tip electrode are in the locked position and, in another instance, can withdraw from the electrode site the entire body assembly less the tip electrode when the weld electrode and the tip electrode are in the unlocked position.

13. In combination, an electrode assembly for a body implantable lead for the delivery of stimulation energy to a desired body site comprising:

a tip electrode having a face adapted for positioning at least adjacent the desired body site;

an elongated electrical conductor;

a longitudinally extending weld electrode having an internal bore, the weld electrode being axially aligned with the tip electrode and at a proximal end engageably receiving one end of the elongated electrical conductor; and a connector member movably mounted on the weld electrode for selective engagement with the tip electrode and, when so engaged, for moving the tip electrode longitudinally between an unlocked position spaced from the weld electrode and a locked position fixed against longitudinal and rotational movement relative to the weld electrode, the connector member including a fastener having an enlarged head and a threaded shank extending away from the enlarged head;

wherein the proximal end of the enlarged head of the fastener is formed with a screwdriver engagement component; and an elongated screwdriver stylet for use with the electrode assembly being selectively engageable with the screwdriver engagement component such that, when so engaged and rotated in one direction, the screwdriver component can move the tip electrode longitudinally between the unlocked position and the locked position and, when rotated in the opposite direction, can move the tip electrode longitudinally between the locked position and the unlocked position.

14. An electrode assembly as set forth in claim 13:

wherein the weld electrode has an outer peripheral surface at its proximal end; and wherein the electrical conductor is a coiled wire strand having a distal end with an inner peripheral surface for fitting reception on the outer peripheral surface of the weld electrode.

15. A combination as set forth in claim 13:

wherein the weld electrode includes an integral weld sleeve with an annular locking tab engageable with the enlarged head to prevent its longitudinal movement with respect to the weld electrode while permitting its rotational movement relative thereto; and wherein the tip electrode includes an integral attachment sleeve having an outer peripheral surface and extending in a direction away from the face thereof, the attachment sleeve having a longitudinally extending tapped bore for threaded engagement with the threaded shank of the connector member.

16. An electrode assembly as set forth in claim 15:

wherein the weld sleeve and the attachment sleeve are mutually stepped to prevent their relative rotation when in the locked position; and wherein when the threaded tip stylet is so engaged with the threaded bore of the weld electrode and drawn in a proximal direction, in one instance, it can withdraw from the body site the entire electrode assembly when the weld electrode and the tip electrode are in the locked position and, in another instance, can withdraw from the body site the entire electrode assembly less the tip electrode when the weld electrode and the tip electrode are in the unlocked position.

* * * * *